United States Patent
DiCarlo

(10) Patent No.: US 8,920,338 B2
(45) Date of Patent: Dec. 30, 2014

(54) BIOPSY DEVICE

(71) Applicant: Boston Scientific Scimed, Inc., Maple Grove, MN (US)

(72) Inventor: Paul D. DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/790,274

(22) Filed: Mar. 8, 2013

(65) Prior Publication Data

US 2013/0190650 A1    Jul. 25, 2013

Related U.S. Application Data

(63) Continuation of application No. 11/456,969, filed on Jul. 12, 2006, now Pat. No. 8,394,033.

(51) Int. Cl.
*A61B 10/02* (2006.01)

(52) U.S. Cl.
CPC ......... *A61B 10/0275* (2013.01); *A61B 10/0266* (2013.01); *A61B 10/0283* (2013.01)
USPC .......................................... 600/567; 600/566

(58) Field of Classification Search
CPC ............. A61B 10/0266; A61B 10/023; A61B 10/0241; A61B 10/02588
USPC ................................................ 600/566, 567
See application file for complete search history.

(56) References Cited

U.S. PATENT DOCUMENTS

| | | | | |
|---|---|---|---|---|
| 3,618,611 A | * | 11/1971 | Urban ........................... | 606/170 |
| 3,732,858 A | * | 5/1973 | Banko ........................... | 600/566 |
| 3,844,272 A | * | 10/1974 | Banko ........................... | 600/566 |
| 4,167,943 A | * | 9/1979 | Banko ........................... | 606/170 |
| 4,368,734 A | * | 1/1983 | Banko ........................... | 606/170 |
| 4,781,202 A | * | 11/1988 | Janese ........................... | 600/567 |
| 5,217,479 A | * | 6/1993 | Shuler ........................... | 606/180 |
| 5,251,641 A | * | 10/1993 | Xavier ........................... | 600/567 |
| 5,526,822 A | * | 6/1996 | Burbank et al. ............... | 600/567 |
| 5,709,698 A | * | 1/1998 | Adams et al. ................. | 606/180 |
| 5,775,333 A | * | 7/1998 | Burbank et al. ............... | 600/567 |
| 5,807,277 A | * | 9/1998 | Swaim ........................... | 600/567 |
| 5,823,970 A | * | 10/1998 | Terwilliger ................... | 600/564 |
| 5,964,716 A | * | 10/1999 | Gregoire et al. .............. | 600/564 |
| 5,989,196 A | * | 11/1999 | Chu et al. ...................... | 600/567 |
| 6,017,316 A | * | 1/2000 | Ritchart et al. ............... | 600/567 |
| 6,139,508 A | * | 10/2000 | Simpson et al. .............. | 600/564 |
| 6,432,064 B1 | * | 8/2002 | Hibner et al. ................. | 600/564 |

(Continued)

FOREIGN PATENT DOCUMENTS

| | | | | |
|---|---|---|---|---|
| DE | 29910783 U1 | * | 9/1999 | ............ A61B 10/00 |
| EP | 1642533 A1 | * | 4/2006 | ............ A61B 10/02 |
| WO | WO 9624289 A2 | * | 8/1996 | ............ A61B 10/00 |
| WO | WO 9734531 A1 | * | 9/1997 | ............ A61B 10/00 |

OTHER PUBLICATIONS

International Preliminary Report On Patentability for International Application No. PCT/US2007/072188 issued on Jan. 13, 2009 (7 pages).

*Primary Examiner* — Sean Dougherty
*Assistant Examiner* — Michael C Stout
(74) *Attorney, Agent, or Firm* — Bookoff McAndrews, PLLC

(57) ABSTRACT

Biopsy devices, as well as related methods and systems, are disclosed.

19 Claims, 14 Drawing Sheets

(56) References Cited

U.S. PATENT DOCUMENTS

| | | | |
|---|---|---|---|
| 6,551,254 B2* | 4/2003 | Nishtalas et al. | 600/567 |
| 6,663,628 B2* | 12/2003 | Peters | 606/45 |
| 6,863,676 B2 | 3/2005 | Lee et al. | |
| 6,981,949 B2 | 1/2006 | Hibner et al. | |
| 7,018,343 B2* | 3/2006 | Plishka | 600/564 |
| 7,033,324 B2* | 4/2006 | Giusti et al. | 600/567 |
| 7,226,424 B2* | 6/2007 | Ritchart et al. | 600/566 |
| 2002/0082519 A1* | 6/2002 | Miller et al. | 600/566 |
| 2003/0229292 A1* | 12/2003 | Hibner et al. | 600/566 |
| 2004/0167427 A1* | 8/2004 | Quick et al. | 600/564 |
| 2004/0260323 A1* | 12/2004 | Truwit et al. | 606/170 |
| 2006/0167377 A1* | 7/2006 | Ritchart et al. | 600/566 |
| 2006/0200040 A1* | 9/2006 | Weikel et al. | 600/566 |
| 2007/0213630 A1* | 9/2007 | Beckman et al. | 600/562 |
| 2007/0255174 A1* | 11/2007 | Hibner | 600/567 |

\* cited by examiner

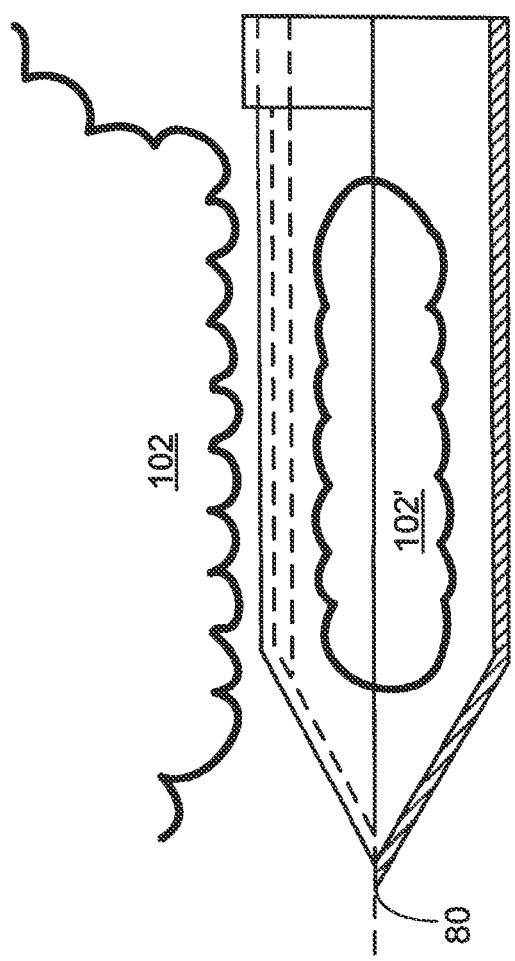
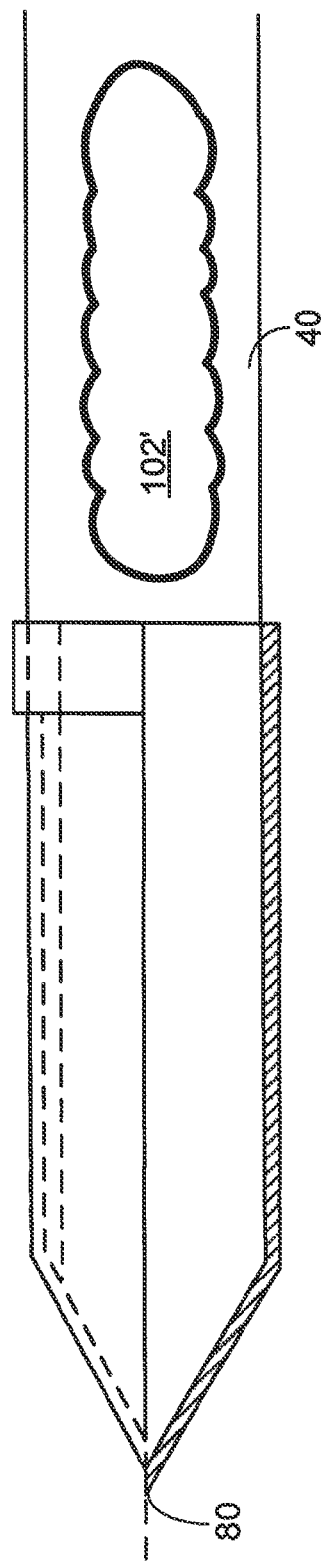
FIG. 9D
FIG. 9E

BIOPSY DEVICE

CROSS-REFERENCE TO RELATED APPLICATIONS

This application is a continuation of and claims the benefit of priority under 35 U.S.C. §120 to U.S. application Ser. No. 11/456,969, filed Jul. 12, 2006, the entire contents of which is hereby fully incorporated by reference.

TECHNICAL FIELD

The invention relates to biopsy devices, and to related methods, components, and systems.

BACKGROUND

Biopsy devices can be used to obtain a tissue specimen from a subject. The tissue specimen can be examined, for example, to determine malignancy.

SUMMARY

The invention relates to biopsy devices, and to related methods, components, and systems.

In one aspect, the invention features a biopsy system that includes a sampling portion defined by first and second components that are moveable relative to each other. In a first position the sampling portion is open, and in a second position the sampling portion is closed. The first component has a wall with a first region and a second region angled relative to the first region of the first component. The second component has a wall with a first region and a second region angled relative to the first region of the second component.

Embodiments can include one or more of the following features.

When in the second position, the first region of the first component and the first region of the second component can form an approximately tubular section. When in the second position, the first and second components can form a tip. When in the first position, the first component can be at least partially disposed within the second component. The second component moves relative to the first component when going from the first position to the second position, and the wall of the second component has an edge configured to cut tissue.

The biopsy device can also include a handpiece and a cannula. The cannula can have proximal and distal ends. The proximal end can be operably coupled with the handpiece, and the distal end can be operably coupled with the sampling portion. The second component can be partially disposed in the cannula, and the second component can be rotatably coupled to the cannula. The first component can be integral with the cannula.

The biopsy device can also include a device configured to form a pressure gradient in the biopsy device. The device can be operatively coupled with the sampling portion so that, during use of the biopsy device, the device forms a pressure gradient in a direction non-parallel to the longitudinal axis of the sampling portion of the biopsy device. In some embodiments, the biopsy device is devoid of a device that forms a pressure gradient in the biopsy device.

The first and second components can be rotatable relative to each other. The biopsy device can have a dead space of less than about five millimeters (e.g., less than about four millimeters, less than about three millimeters, less than about one millimeter).

In an additional aspect, the invention features a biopsy device that includes a sampling portion and a device configured to form a pressure gradient in the biopsy device. The sampling portion has a longitudinal axis. The device is operatively coupled with the sampling portion so that, during use of the device, the device forms a pressure gradient in a direction non-parallel to the longitudinal axis of the sampling portion.

Embodiments can include one or more of the following features.

The non-parallel direction can be a direction substantially perpendicular to the longitudinal axis of the sampling portion. The first device can be configured so that, during use of the first device, the first device draws tissue into the sampling portion.

The biopsy device of can include a second device configured to form a pressure gradient in the biopsy device. The second device can be operatively coupled with the sampling portion so that, during use of the second device, the second device forms a pressure gradient in a direction substantially parallel to the longitudinal axis of the sampling portion.

The sampling portion of the biopsy device can include first and second components rotatable relative to each other. The second component can move relative to the first component when going from a first position in which sampling portion is open to a second position in which the sampling portion is closed. A wall of the second component can have an edge configured to cut tissue.

The second component can include at least one orifice that provides fluid communication between an interior of the sampling portion and the first device. The biopsy device can also include a handpiece and a cannula. The cannula can have proximal end and distal ends. The proximal end can be operably coupled with the handpiece and the distal end can be operably coupled with the sampling portion. The sampling portion can include first and second components rotatable relative to each other. The second component can be partially disposed in the cannula and rotatably coupled to the cannula. The first component can be integral with the cannula. The biopsy device can have a dead space of less than about five millimeters (e.g., less than about four millimeters, less than about three millimeters, less than about one millimeter).

In an additional aspect, the invention features a biopsy device that includes a handpiece, a cannula, and a sampling portion. The cannula is operatively coupled with the handpiece and has a distal end. The sampling portion of the biopsy device is operatively coupled with the distal end of the cannula. The sampling portion includes a first component and a second component that is moveable relative to the first component. In a first position the sampling portion is closed and in a second position the sampling portion is open.

Embodiments can include one or more of the following features.

When in the first position, the first component and the second component can form a substantially closed portion having a tubular region and a tip region. When in the second position, the first component can be at least partially disposed within the second component. The first component can include a first portion having a semi-circular cross-section and a second portion extending at a non-right angle from the first portion of the first component to form a tip. The second component can include a first portion having a semi-circular cross-section and a second portion extending at a non-right angle from the first portion of the second component to form a tip. The first portion of the first and second portions of the first component can include an edge configured to cut tissue.

The biopsy device can include a first device configured to form a pressure gradient in the biopsy device. The first device can be in fluid communication with at least one orifice in the sampling portion so that, during use of the first device, the first device forms a pressure gradient in a direction non-parallel to a longitudinal axis of the sampling portion. The biopsy device can include a second device configured to form a pressure gradient in the biopsy device. The second device can be operatively coupled with the sampling portion so that, during use of the second device, the second device forms a pressure gradient in a direction substantially parallel to the longitudinal axis of the sampling portion.

The biopsy device can have a dead space of less than about five millimeters (e.g., less than about four millimeters, less than about three millimeters, less than about one millimeter).

In an additional aspect, the invention features a biopsy device that includes a sampling portion having two components that are rotatable relative to each other. The biopsy device has a dead space of less than about five millimeters (e.g., less than about four millimeters, less than about three millimeters, less than about one millimeter).

Embodiments can have one or more of the following advantages.

In some embodiments, a biopsy device can be designed to increase the sample size of a sample retrieved by biopsy device. This can be advantageous because a larger sample provides more tissue for testing and/or fewer samples may be required.

In certain embodiments, a biopsy device can be designed to reduce the dead space of the biopsy device. This can be beneficial because a reduction in dead space can allow for more accurate positioning of the biopsy device.

In some embodiments, a biopsy device can be configured to form a pressure gradient in a sampling portion. This can be desirable because it can, for example, increase the sample size of a sample retrieved by the biopsy device.

Features and advantages are in the description, drawings, and claims.

DESCRIPTION OF DRAWINGS

FIGS. 9A-9E illustrate the use of a biopsy device to sample tissue.

DETAILED DESCRIPTION

Figure 1:
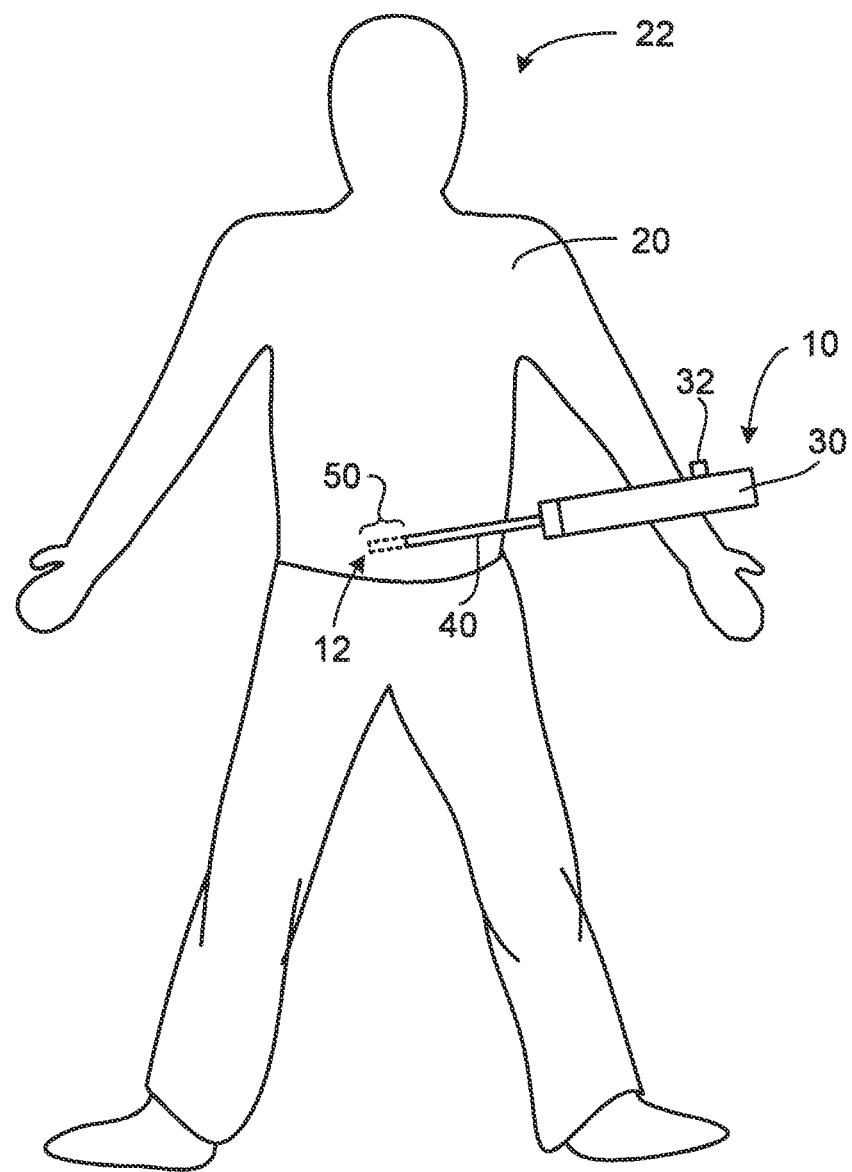
FIG. 1 illustrates the delivery of a portion of a biopsy device into the body of a subject.

FIG. 1 shows biopsy device 10 being used in the body 20 of a subject 22. As shown in FIG. 1, distal end 12 of biopsy device 10 is inserted into body 20. Biopsy device 10 can be used, for example, to obtain specimens of soft tissue (e.g., lung, kidney, liver, breast, thyroid, adrenal glands, endometrial, muscle, myocardial, and lymphatic), to obtain specimens of hard lesions (e.g., hard cancerous lesions, malignant tumors such as lipomas and liposarcoma), and to obtain specimens of bone. As described below, during use of biopsy device 10, biopsy device 10 is activated which causes biopsy device 10 to dissect a specimen.

Figure 2:
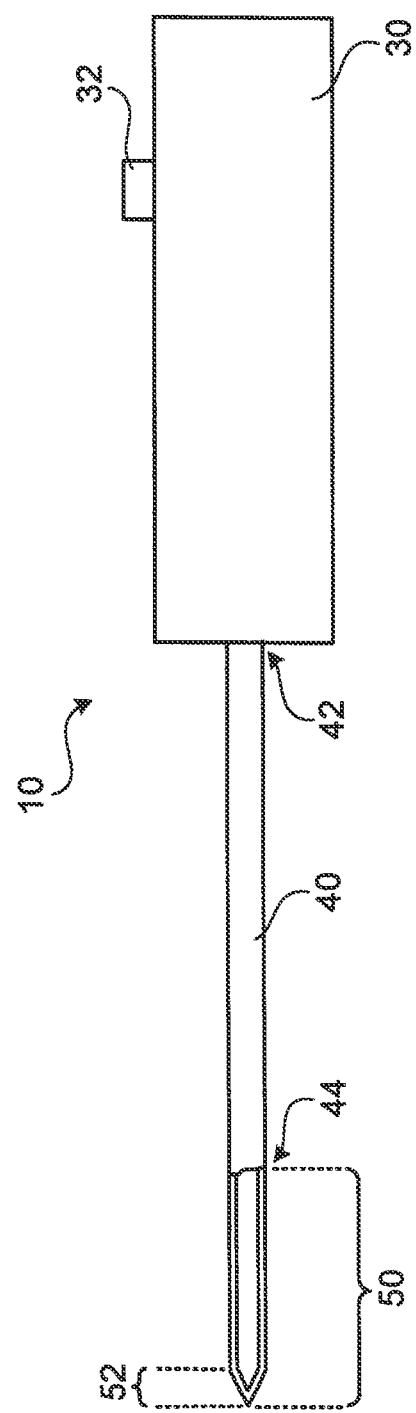
FIG. 2 is a side view of an embodiment of a biopsy device.
Figure 3A:
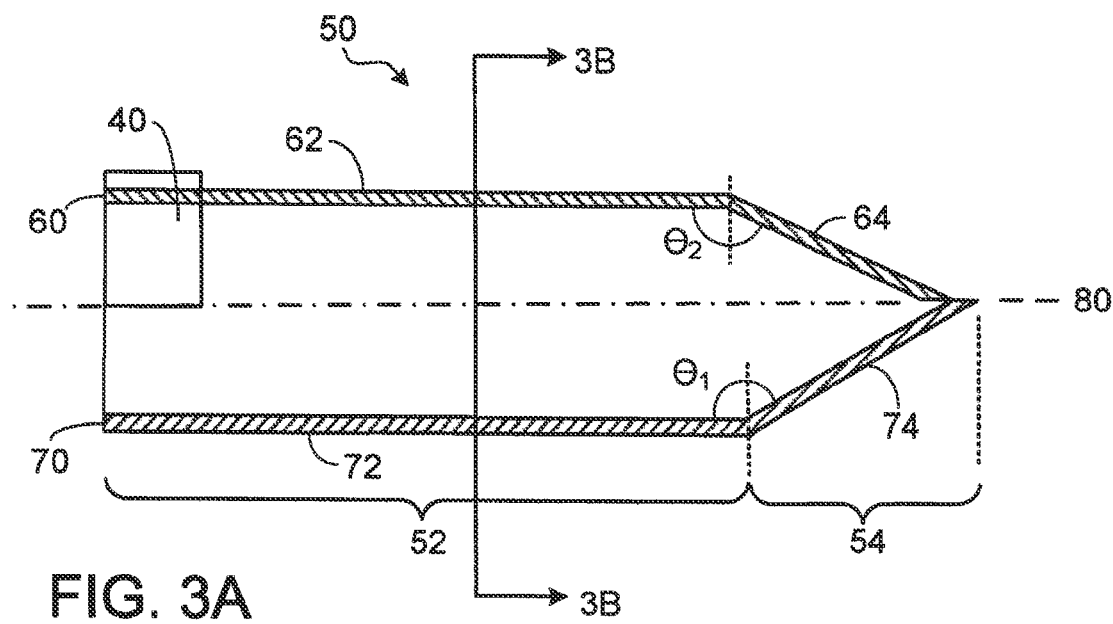
FIG. 3A is a side cross-sectional view of an embodiment of a biopsy device.

As shown in FIG. 2, biopsy device 10 includes a handpiece 30, a cannula 40, and a sampling portion 50. Handpiece 30 includes an activation button 32 which can be used to actuate sampling portion 50 between an open position and a closed position (as described below). A proximal end 42 of cannula 40 is connected to a distal end of handpiece 30. Cannula 40 is generally a hollow sheath, e.g., made of stainless steel. Sampling portion 50 of biopsy device 10 is connected to a distal end 44 of cannula 40. Sampling portion 50 includes a pointed distal end 52. During use, sampling portion 50 and at least a portion of cannula 40 are inserted into a subject (e.g., a human subject) to retrieve a specimen.

FIGS. 3A-B and 4A-B show sampling portion 50 of biopsy device 10 in the closed and open positions, respectively. Biopsy device 10 can be actuated between the closed and open positions in order to retrieve a sample. For example, in some embodiments, the biopsy device 10 is placed in the closed position during insertion. Since the biopsy device 10 is in the closed position upon insertion, the biopsy device 10 is actuated to the open position after insertion. Tissue is drawn into the sampling portion of biopsy device 10 (e.g., via suction) and the biopsy device 10 is actuated from the open position to the closed position to cut the tissue.

Sampling portion 50 includes an inner component 60 and an outer component 70. Inner component 60 is moveable relative to outer component 70. For example, inner component 60 can rotate about an axis 80 relative to outer component 70. In the closed position, outer component 70 and inner component 60 form a tubular region 52 and a tip region 54 (e.g., a cone-shaped tip region). In the open position, inner component 60 is disposed within outer component 70 forming a sampling region 56. Inner component 60 includes a sharp edge 65 that is configured to sever tissue when inner component 60 is rotated from the open position to the closed position.

Outer component 70 includes a tubular region 72 and a tip region 74. Tubular region 72 includes a distal end connected at an angle with tip region 74 and a proximal end connected to cannula 40 (FIG. 2). Outer component 70 can be integral with cannula 40. For example, in some embodiments, outer component 70 and cannula 40 can be formed as a unitary piece. In some additional embodiments, outer component 70 and cannula 40 can be formed as separate pieces and bonded together (e.g., outer component 70 can be welded to cannula 40).

Similarly, inner component 60 includes a tubular region 62 and a tip region 64. Tubular region 62 includes a distal end connected at an angle with tip region 64 and a proximal end moveably coupled to cannula 40.

Inner component 60 can be moveably coupled (e.g., rotatably coupled) to cannula 40 using any desired method. In certain embodiments, inner component 60 is rotatable by from about 170° to about 190° (e.g., about 180°) such that edge 65 can completely sever tissue when rotating between the open position and the closed position.

Edge 65 is present on both tubular region 62 and a tip region 64 of inner component 60. When rotated between the open and closed positions, edge 65 severs tissue in both tubular region 52 and tip region 54 of biopsy device 10. Providing edge 65 along both tubular region 62 and a tip region 64 of inner component 60 can provide various advantages such as, for example, increasing the sample size of a sample retrieved by biopsy device 10 and/or reducing the dead space (e.g., the length of device 10 that extends beyond the portion of tissue being sampled) of biopsy device 10.

Figure 4A:
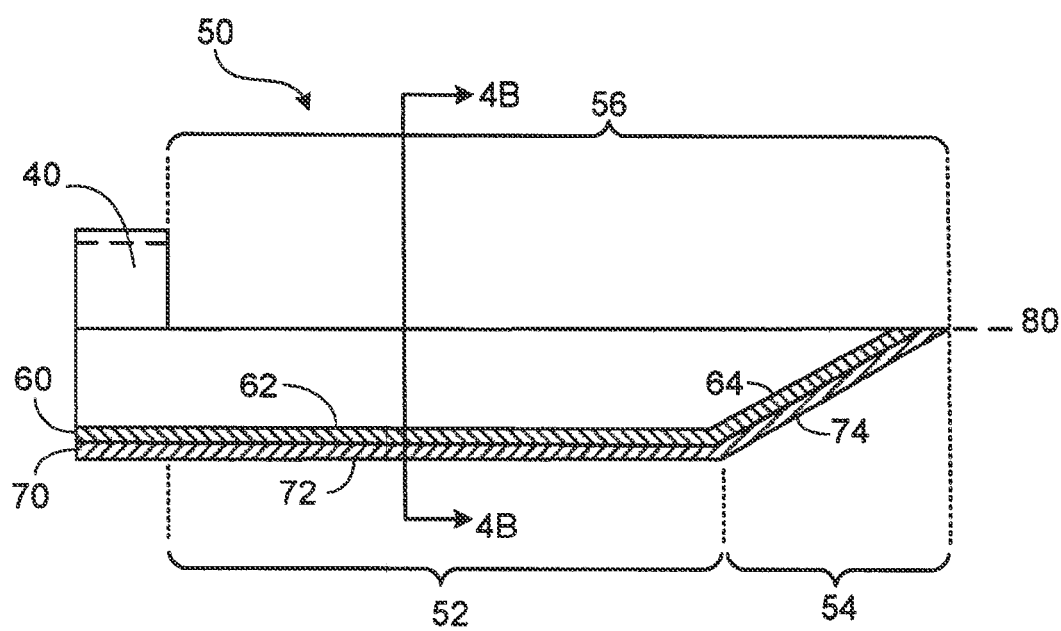
FIG. 4A is a side cross-sectional view of an embodiment of a biopsy device.
Figure 3B:
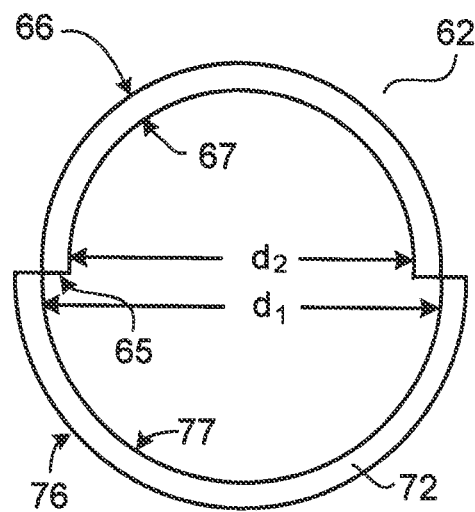
FIG. 3B is a cross-sectional view of the biopsy device of FIG. 3A, taken along line 3B-3B in FIG. 3A.
Figure 4B:
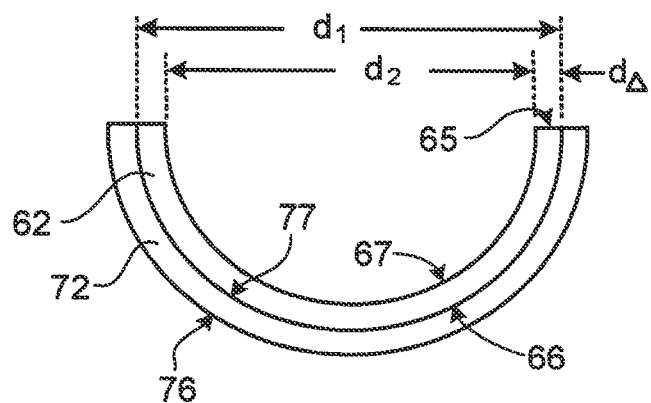
FIG. 4B is a cross-sectional view of the biopsy device of FIG. 4A, taken along line 4B-4B in FIG. 4A.

As shown in FIGS. 3B and 4B, tubular region 72 of outer component 70 and tubular region 62 of inner component 60 are generally curved in shape, for example semi-circular. Tubular region 72 includes an inner wall 77 and an outer wall 76. The diameter, $d_1$, of tubular region 72 (measured as the distance between the inner walls at the opening of tubular region 72) can be selected as desired. In some embodiments, diameter $d_1$ of tubular region 72 can be at least about 0.5 millimeter (e.g., at least about 1 millimeter, at least about 3 millimeters, at least about 5 millimeters, about 7 millimeters, about 10 millimeters, about 12 millimeters) and/or at most about 15 millimeters (e.g., at most about 12 millimeters, at least most 10 millimeters, at most 7 millimeters, at most 5 millimeters, at most 3 millimeters).

Tubular region 62 includes an inner wall 67 and an outer wall 66. The diameter ($d_2$) of tubular region 62 (measured as the distance between the inner walls at the opening of tubular region 62) can be selected as desired. For example, diameter $d_2$ can be selected based on a desired sample size. In some embodiments, diameter $d_2$ of tubular region 62 can be at least about 0.5 millimeter (e.g., at least about 1 millimeter, at least about 3 millimeters, at least about 5 millimeters, about 7 millimeters, about 10 millimeters, about 12 millimeters) and/ or at most about 15 millimeters (e.g., at most about 12 millimeters, at least most 10 millimeters, at most 7 millimeters, at most 5 millimeters, at most 3 millimeters).

In general, diameter $d_2$ is less than diameter $d_1$. The difference between diameter $d_2$ and diameter $d_1$ allows inner component 60 to fit within outer component 70 when biopsy device 10 is in the open position (FIG. 4A). For example, the difference between diameter $d_2$ and diameter $d_1$ can be from about 1 millimeter to about 10 millimeters (e.g., from about 0.2 millimeter to about 0.8 millimeter, from about 0.4 millimeter to about 0.6 millimeter, about 3 millimeters, about 5 millimeters, about 7 millimeters). In the open position, inner component 60 is disposed within outer component 70 such that inner wall 77 of tubular region 72 is adjacent to outer wall 66 of tubular region 62. In the closed position, inner component 60 and outer component 70 form a closed structure.

As described above, tip region 74 of outer component 70 and tip region 64 of inner component 60 can be adapted to penetrate tissue (e.g., in the body of a subject). Tip region 74 is angled relative to tubular region 72. For example, tip region 74 can be disposed at an angle $\theta_1$ relative to tubular region 72 where $\theta_1$ is greater than about 90° and less than about 180°. In some embodiments, $\theta_1$ is from about 110° to about 160° (e.g., from about 120° to about 150°, from about 130° to about 140°, from about 133° to about 137°, about 135°). Generally, tip region 74 can be connected to tubular region 72 using any desired method. In some embodiments, tip region 74 and tubular region 72 may be formed as a unitary piece. In certain embodiments, tip region 74 and tubular region 72 may be separately formed and then bonded together.

Tip region 64 is angled relative to tubular region 62. For example, tip region 64 can be disposed at an angle $\theta_2$ relative to tubular region 62 where $\theta_2$ is greater than about 90° and less than about 180°. Preferably, $\theta_2$ is from about 110° to about 160° (e.g., from about 120° to about 150°, from about 130° to about 140°, from about 133° to about 137°, about 135°). Generally, $\theta_2$ is approximately the same as $\theta_1$ such that in a closed position (FIG. 3A) tip region 74 and tip region 64 form a closed, pointed tip region 54. Tip region 64 can be connected to tubular region 62 using any desired method. In some embodiments, tip region 64 and tubular region 62 may be formed as a unitary piece. In certain embodiments, tip region 64 and tubular region 62 may be separately formed and then bonded together.

Figure 5:
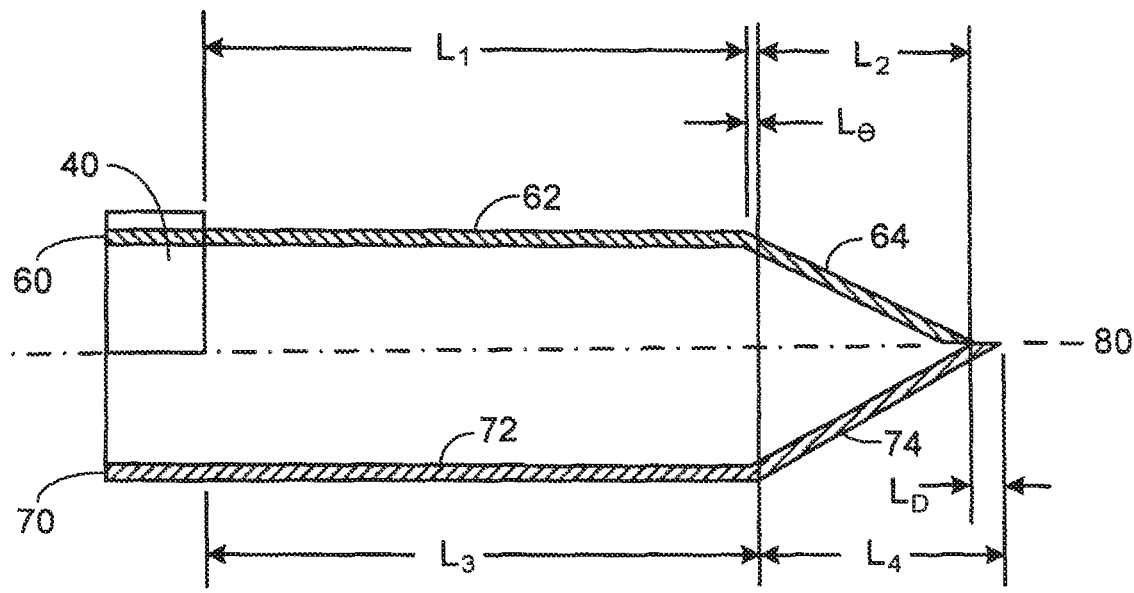
FIG. 5 is a side cross-sectional view of an embodiment of a biopsy device.

As shown in FIG. 5, tubular region 62 of inner component 60 has a length $L_1$ and tip region 64 of inner component 60 has a length $L_2$. Tubular region 72 of outer component 70 has a length $L_3$ and tip region 74 of outer component 70 has a length $L_4$. Lengths $L_1$, $L_2$, $L_3$, and $L_4$ can be selected as desired.

In certain embodiments, length $L_1$ can be at least about one millimeter (e.g., at least about three millimeters, at least about five millimeters, at least about seven millimeters, at least about ten millimeters, at least about fifteen millimeters), and/ or at most about twenty millimeters (e.g., at most about fifteen millimeters, at most about ten millimeters, at most about seven millimeters, at most about five millimeters, at most about three millimeters). In certain embodiments, length $L_2$ can be at least about one millimeter (e.g., at least about three millimeters, at least about five millimeters, at least about seven millimeters, at least about ten millimeters), and/or at most about fifteen millimeters (e.g., at most about ten millimeters, at most about seven millimeters, at most about five millimeters, at most about three millimeters).

In certain embodiments, length $L_3$ can be at least about one millimeter (e.g., at least about three millimeters, at least about five millimeters, at least about seven millimeters, at least about ten millimeters, at least about fifteen millimeters), and/ or at most about twenty millimeters (e.g., at most about fifteen millimeters, at most about ten millimeters, at most about seven millimeters, at most about five millimeters, at most about three millimeters). In certain embodiments, length $L_4$ can be at least about one millimeter (e.g., at least about three millimeters, at least about five millimeters, at least about seven millimeters, at least about ten millimeters), and/or at most about fifteen millimeters (e.g., at most about ten millimeters, at most about seven millimeters, at most about five millimeters, at most about three millimeters).

In general, length $L_1$ is about the same as length $L_3$. For example, in certain embodiments, the difference ($L_\theta$) between length $L_1$ and length $L_3$ can be at most about 2 millimeters (e.g., at most about 1.5 millimeters, at most about 1.25 millimeters, at most about 1.0 millimeter, at most about 0.75 millimeter, at most about 0.5 millimeter). In addition, length $L_2$ is about the same as to length $L_4$. For example, in certain embodiments, the difference ($L_D$) between length $L_2$ and length $L_4$ can be at most about 2 millimeters (e.g., at most about 1.5 millimeters, at most about 1.25 millimeters, at most about 1.0 millimeter, at most about 0.75 millimeter, at most about 0.5 millimeter).

Since the length of inner component 60 and outer component 70 are about the same, the dead space ($L_D$) of biopsy device 10 is reduced. The dead space of biopsy device 10 refers to the length of device 10 that extends beyond the portion of tissue being sampled. As shown in FIG. 5, the dead space, $L_D$, is the difference between the length of inner component 60 ($L_1+L_2$) and the length of outer component 70 ($L_3+L_4$). In certain embodiments, the dead space of biopsy device 10 is less than about ten millimeters (e.g., less than about seven millimeters, less than about five millimeters, less than about four millimeters, less than about three millimeters, less than about two millimeters, less than about one millimeter).

Figure 6:
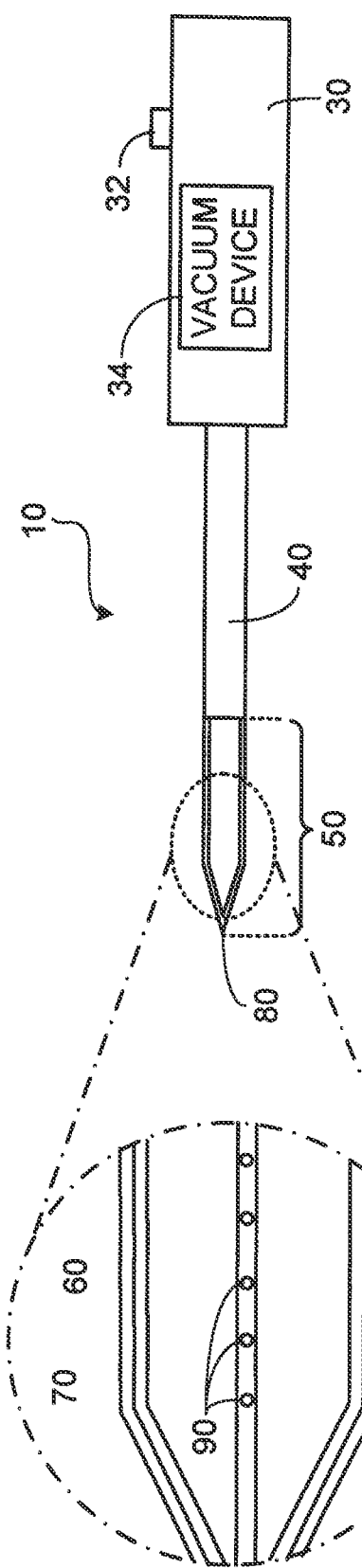
FIG. 6 is a cross-sectional view of an embodiment of a biopsy device and an enlarged region of a portion of the biopsy device.
Figure 7:
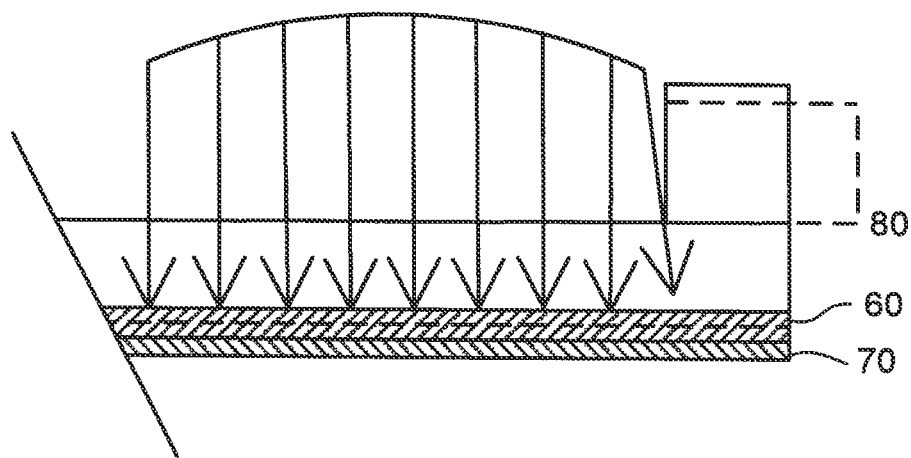
FIG. 7 is a partial side cross-sectional view of a portion of a biopsy device.

In some embodiments, a pressure gradient can be used to draw tissue into sampling portion 50 of biopsy device 10. For example, FIG. 6 shows an embodiment of biopsy device 10 in which biopsy device 10 includes a vacuum device 34 configured to form a pressure gradient in sampling portion 50. Vacuum device 34 is in fluid communication with one or more orifices 90 located in inner component 60. During use, vacuum device 34 applies a vacuum to orifices 90 such that the pressure gradient is formed in a direction non-parallel to the longitudinal axis 80 of sampling portion 50 (e.g., as shown in FIG. 7). For example, in certain embodiments, the pressure gradient can be formed at an angle that is at least about 10° (e.g., at least about 25°, at least about 45°, at least about 60°, at least about 75°, at least about 85°) with respect to longitudinal axis 80. In some embodiments, the pressure gradient can be at an angle that is substantially perpendicular (at least about 85° with respect to) longitudinal axis 80.

Figure 8A:
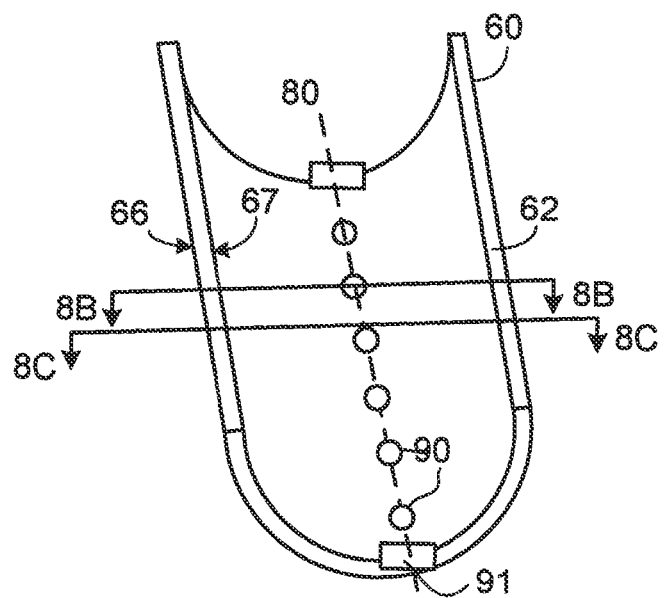
FIG. 8A is a perspective view of a component of the biopsy device.
Figure 8B:
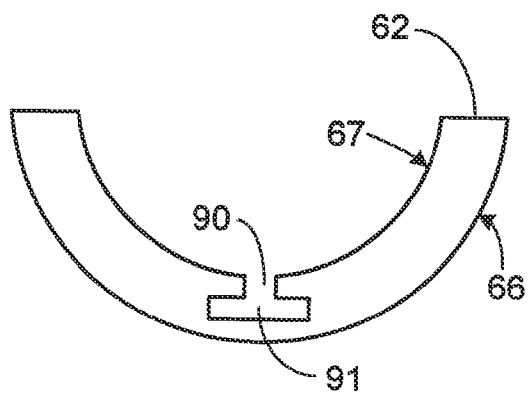
FIG. 8B is a cross-sectional view of the component of FIG. 8A, taken along line 8B-8B in FIG. 8A.
Figure 8C:
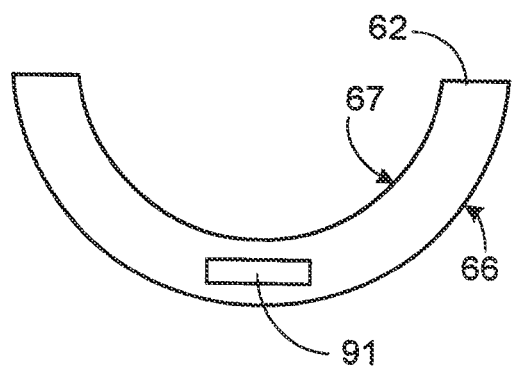
FIG. 8C is a cross-sectional view of the component of FIG. 8A, taken along line 8C-8C in FIG. 8A.

FIG. 8A shows a perspective view of inner component 60 of a biopsy device 10 which includes multiple orifices 90. FIGS. 8B and 8C show cross-sectional views of inner component 60 at locations 8B-8B and 8C-8C, respectively. Inner component 60 includes multiple orifices 90 arranged along longitudinal axis 80 of inner component 60. In order to form a pressure gradient, vacuum device 34 applies a vacuum to orifices 90. For example, orifices 90 can be in fluid communication with vacuum device 34 by a hollow region 91 between inner wall 67 and outer wall 66 of inner component 60.

Figure 9A:
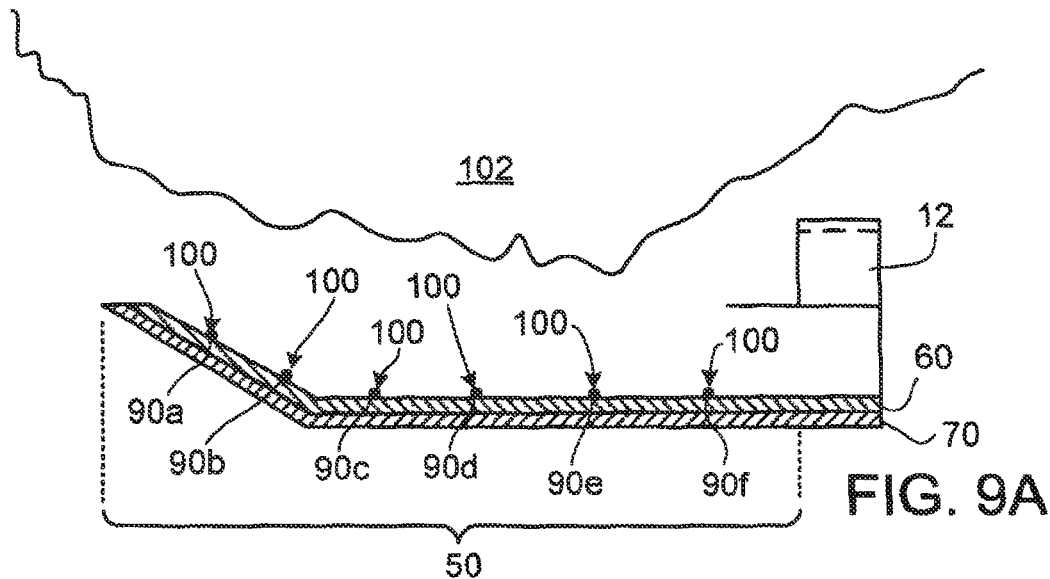
Figure 9B:
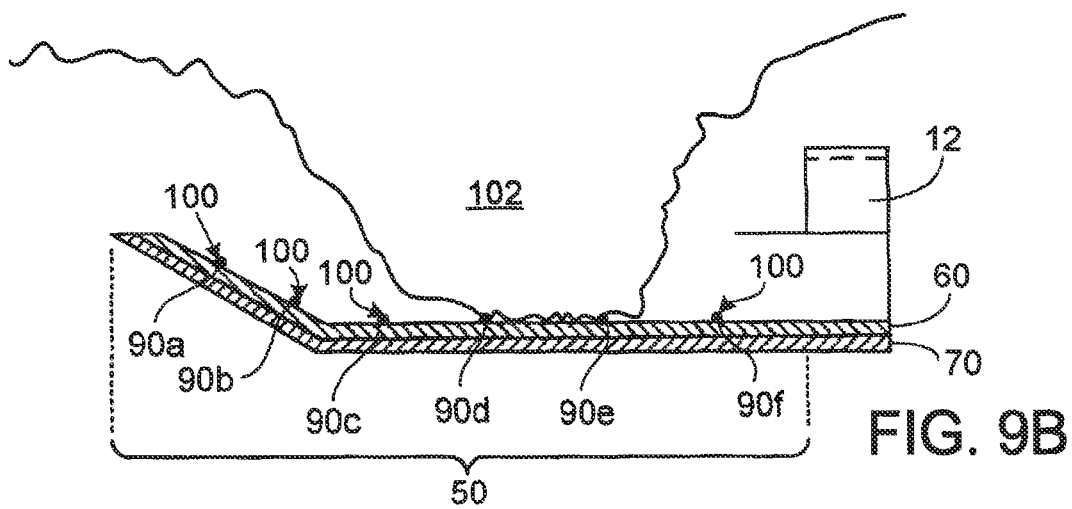
Figure 9C:
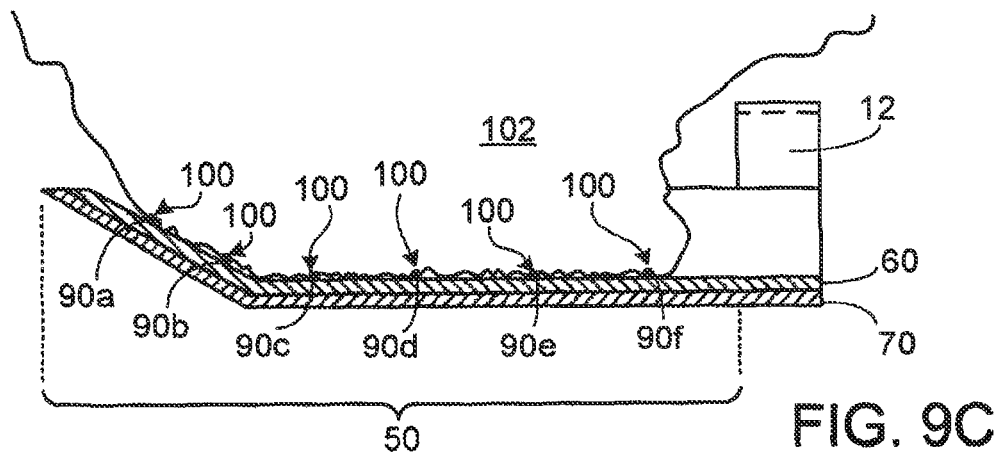

FIGS. 9A-9E illustrate the use of biopsy device 10. FIG. 9A shows an exemplary sampling device in which inner component 60 includes multiple orifices (e.g., orifices 90a, 90b, 90c, 90d, 90e, and 90f). A pressure gradient can be formed in sampling portion 50 by applying a vacuum to orifices 90a, 90b, 90c, 90d, 90e, and 90f (as indicated by arrows 100). As shown in FIG. 9B the pressure gradient draws tissue 102 into sampling portion 50. As tissue 102 is drawn into sampling portion 50, portions of tissue 102 can come into physical contact with inner component 60. When tissue 102 comes into contact with inner component 60, tissue 102 can block one or more of the orifices (e.g., orifices 90a, 90b, 90c, 90d, 90e, and 90f) which form the pressure gradient. As shown in FIG. 9B, tissue 102 has prolapsed such that orifices 90d and 90e are covered. When orifices 90d and 90e become covered, the pressure gradient applied by the other orifices (e.g., orifices 90a, 90b, 90c, and 90f) increases helping to draw additional tissue 102 into sampling portion 50 thereby increasing the sample size of tissue 102 (FIG. 9C). After the tissue 102 has been drawn into sampling portion 50, inner component 60 is rotated relative to outer component 70 shearing the portion of tissue 102 that has been drawn into sampling portion 50 to form a tissue specimen 102' (FIG. 9D). The tissue specimen 102' is drawn into cannula 40 by applying a pressure gradient in a direction substantially parallel to longitudinal axis 80 of sampling portion 50 (FIG. 9E).

Figures 10, 11:
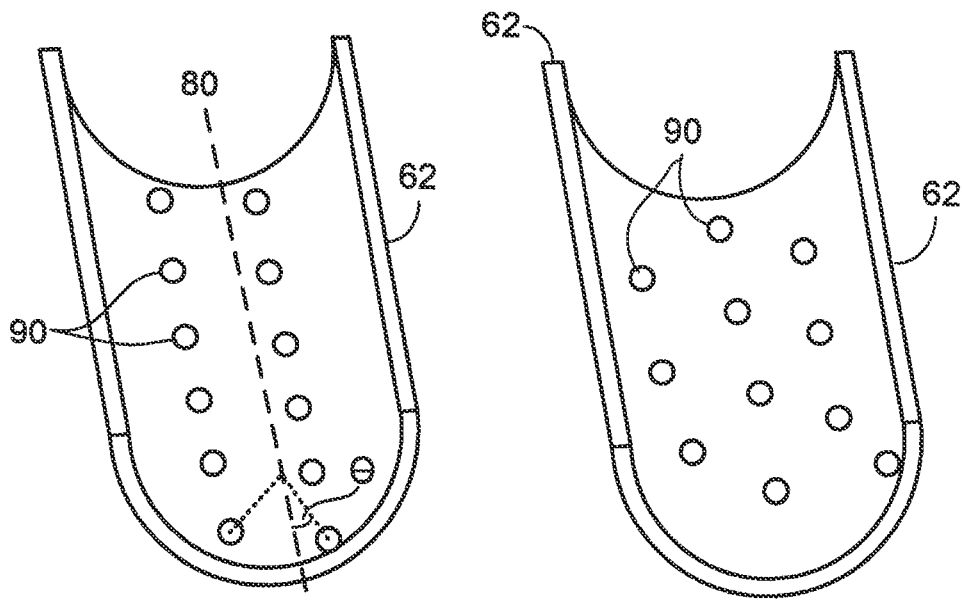
FIG. 10 is a perspective view of a component of the biopsy device.
FIG. 11 is a perspective view of a component of the biopsy device.

While in the example described above, orifices 90 were arranged along a longitudinal axis 80 of inner component 60, orifices 90 can be arranged as desired. For example, multiple sets of orifices (e.g., two sets, three sets, four sets, five sets) can be arranged in a configuration offset from the longitudinal axis 80 by an angle θ. For example, θ can be from about 5° to about 80° (e.g., about 10°, about 15°, about 30°, about 45°, about 60°). FIG. 10 shows an exemplary arrangement of two sets of orifices disposed at an angle θ of about +/−30 degrees from longitudinal axis 80. FIG. 11 shows an additional exemplary arrangement of orifices 90 in which orifices 90 are randomly spaced within inner component 60.

Figure 12:
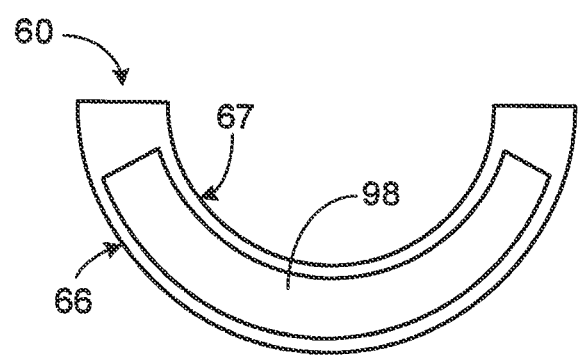
FIG. 12 is a cross-sectional view of a portion of a biopsy device.

While in the embodiments described above a hollow tube 91 was in fluid communication with the orifices, as shown in FIG. 12, in some additional embodiments, the entire region 98 between inner wall inner wall 67 and outer wall 66 of inner component 60 could be hollow.

Figure 13:
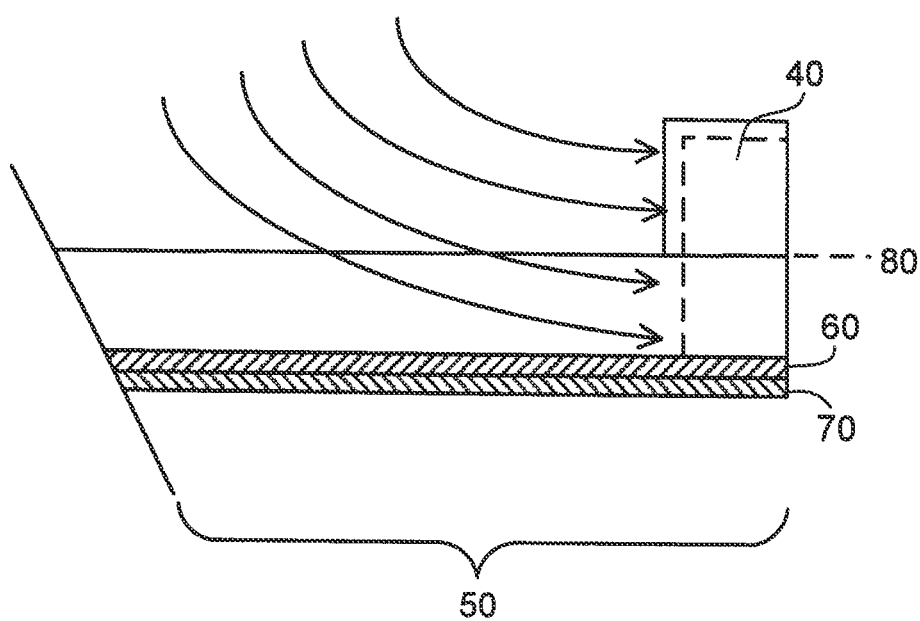
FIG. 13 is a partial side cross-sectional view of a portion of a biopsy device.

In certain embodiments, as shown in FIG. 13, biopsy device 10 can include an additional pressure gradient applied in a direction substantially parallel to (at most about 5° with respect to) longitudinal axis 80 of sampling portion 50. In embodiments that include pressure gradients in both parallel and non-parallel directions, the pressure gradient in the non-parallel direction (FIG. 7) can be used to draw tissue into sampling portion 50 prior to severing the sample while the pressure gradient in the parallel direction (FIG. 13) can be used to draw a severed sample into cannula 40 of biopsy device 10.

Figure 14A:
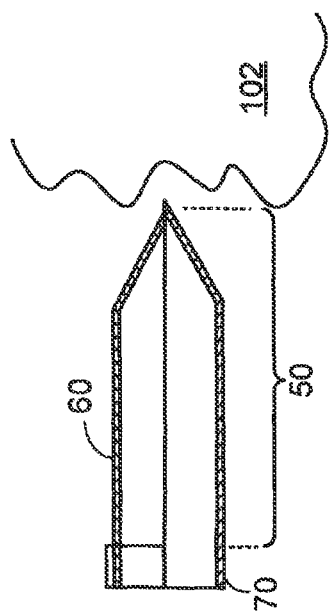
FIGS. 14A-14D illustrate the use of a biopsy device to sample tissue.
Figure 14B:
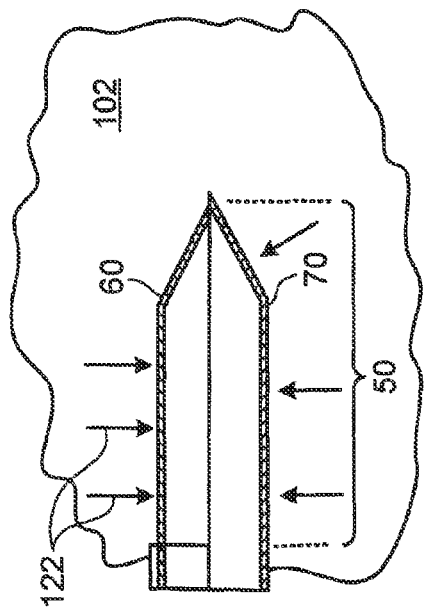
Figure 14C:
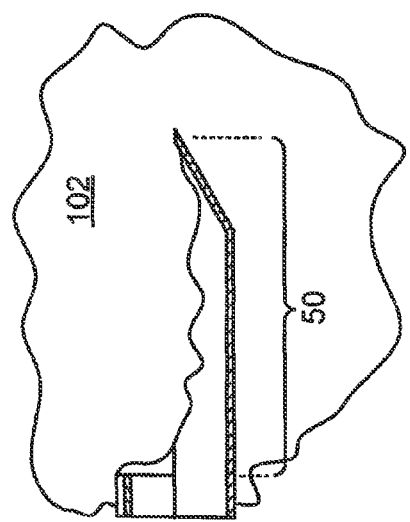
Figure 14D:
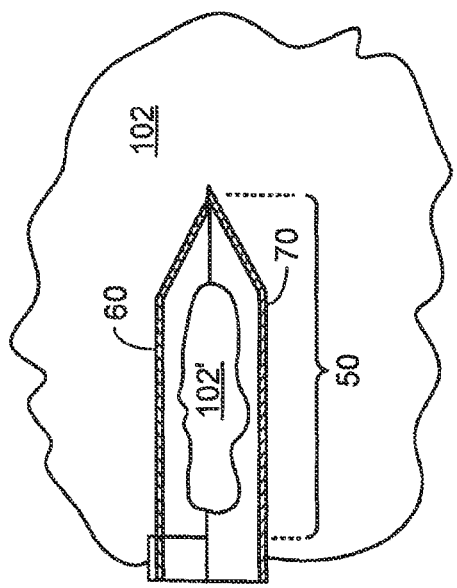

While in some of the embodiments described above biopsy device 10 forms a pressure gradient to draw tissue into sampling portion 50, in certain embodiments biopsy device 10 is devoid of a device that forms a pressure gradient in sampling portion 50. For example, FIGS. 14A-14D illustrate the use of a biopsy device 10 without application of a pressure gradient. Prior to insertion of biopsy device 10 into the body, sampling portion 50 is placed in a closed position (FIG. 14A). Sampling portion 50 and at least a portion of cannula 40 are inserted into the subject's body such that sampling portion 50 extends into a tissue 102 (FIG. 14B). When sampling portion 50 is disposed in tissue 102, tissue 102 is displaced from a relaxed position forming a pressure on the outer walls of sampling portion 50 as indicated by arrows 122. Sampling portion 50 is actuated into an open position by rotation of inner component 60 (FIG. 14C). Upon rotation of inner component 60 into the open position, a portion of the tissue 102 prolapses into sampling portion 50. Inner component 60 is subsequently rotated relative to outer component 70 such that edge 65 shears the portion of tissue 102 that had prolapsed into sampling portion 50 (FIG. 14D) thereby forming a tissue specimen 102'.

While certain embodiments have been described, other embodiments are possible.

For example, the components of biopsy device 10 described above can be formed by conventional injection molding techniques, e.g., of polycarbonate and/or ABS.

As a further example, in certain embodiments, sampling portion 50 and cannula 40 can be formed of stainless steel.

As a further example, in some embodiments, a medical kit can include a biopsy handpiece 30, multiple cannulas 40 and sampling portions 50 (e.g., having different lengths).

As an additional example, in certain embodiments, a portion of the sampling portion 50 and/or cannula can be configured to cauterize tissue. For example, an electrocautery material can be added to a portion of sampling portion 50 (e.g., the tip) and an insulation can be placed on the remainder of sampling portion 50 and on cannula 40. The electrocautery feature allows the biopsy device 10 to cauterize tissue and stop bleeding.

Figure 15A:
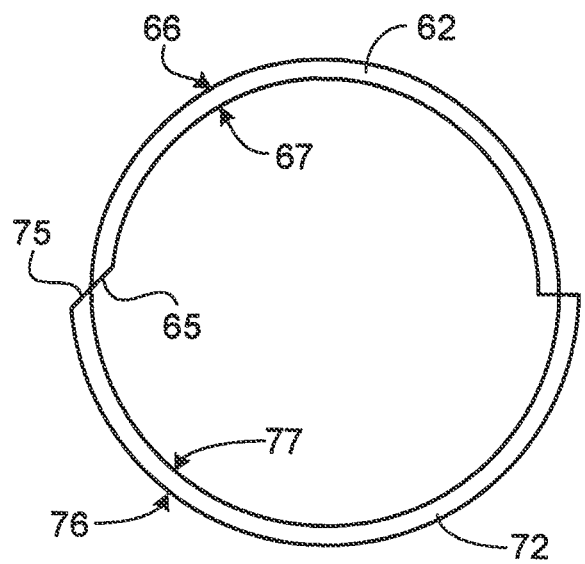
FIG. 15A is a cross-sectional view of the biopsy device.
Figure 15B:
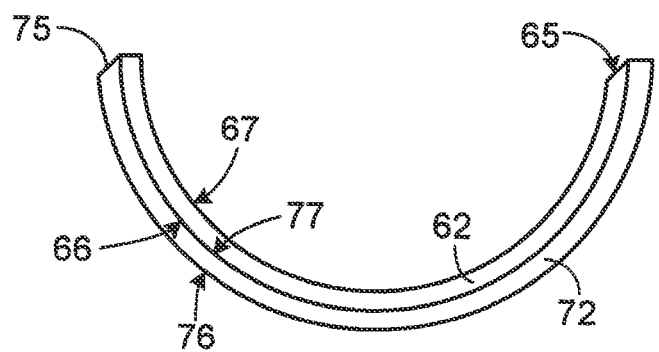
FIG. 15B is a cross-sectional view of the biopsy device.

As an additional example, while embodiments described above (e.g., as shown in FIGS. 3B and 4B) describe an edge 65 that extends at an angle from inner wall 67 and outer wall 66 to form a sharp edge at a location between inner wall 67 and outer wall 66 of inner component 60, other methods for forming the sharp edge 65 can be used. For example, as shown in FIGS. 15A and 15B, the sharp edge 65 can extend from inner wall 67 to outer wall 66. As described above, when rotated between the open and closed positions, edge 65 severs tissue in tubular region 52 and tip region 54 of biopsy device 10.

As an additional example, in certain embodiments, both inner component 60 and outer component 70 can include a sharp edge that is configured to sever tissue when inner component 60 is rotated from the open position to the closed position. For example, as shown in FIGS. 15A and B, inner component 60 can include an edge 65 is present on both tubular region 62 and a tip region 64 of inner component 60 and outer component 70 can include an edge 75 that is present in tubular region 72 and a tip region 74 of inner component 70. In some embodiments, edge 65 of component 60 can extend at an angle from inner wall 67 to outer wall 66 and edge 75 can extend at an angle from inner wall 77 to outer wall 76. When rotated between the open and closed positions, edges 65 and 75 sever tissue in both tubular region 52 and tip region 54 of biopsy device 10.

Other embodiments are in the claims.

What is claimed is:

1. A method of obtaining a tissue sample, comprising:
positioning a sampling portion of a biopsy device proximate target tissue, wherein the sampling portion is configured to receive and sever tissue, the sampling portion extending along a longitudinal axis;
moving the sampling portion from a closed position to an open position by moving a moveable member relative to a stationary member, the moveable member having a sharp edge, a hollow channel therein, a plurality of orifices in fluid communication with the hollow channel, and a tip portion configured to pierce tissue, wherein in the open position at least two of the plurality of orifices are offset on either side of a central longitudinal axis of the moveable member, wherein in the open position, the moveable member is configured to be received by and nest within the stationary member, wherein the moveable member includes a cross-sectional shape of a partial circle complimentary to a partial circle cross-sectional shape of the stationary member;
receiving tissue within the moveable member; and
applying a pressure differential in the sampling portion via a pressure differential system, the pressure differential system being configured to form a pressure differential in the sampling portion when the sampling portion is in the open position, wherein the pressure differential system is in fluid communication with the hollow channel and the plurality of orifices of the moveable member.

2. The method of claim 1, wherein applying a pressure differential includes applying a pressure differential in a direction substantially perpendicular to the longitudinal axis.

3. The method of claim 2, wherein the pressure differential is a first pressure differential, the method further including:
applying a second pressure differential in the sampling portion via the pressure differential system, the pressure differential system being configured to form the second pressure differential in the sampling portion when the sampling portion is in the open position, wherein the second pressure differential is in a direction substantially parallel to the longitudinal axis.

4. The method of claim 1, wherein the moveable member further includes an elongate portion, stationary member includes an elongate portion and a tip portion, and wherein the sharp edge of the moveable member extends along the elongate portion and the tip portion of the moveable member.

5. The method of claim 4, wherein the stationary member includes a sharp edge extending along the elongate portion and the tip portion of the stationary member.

6. The method of claim 1, further including:
moving the sampling portion from the open position to the closed position and severing tissue.

7. The method of claim 1, wherein moving the sampling portion from a closed position to an open position includes rotating the moveable member about the longitudinal axis.

8. A method of obtaining a tissue sample, comprising:
positioning a sampling portion of a biopsy device proximate target tissue, wherein the sampling portion is configured to receive and sever tissue, the sampling portion extending along a longitudinal axis;
moving the sampling portion from a closed position to an open position by rotating a moveable member about the longitudinal axis and relative to a stationary member, wherein each of the moveable and stationary members includes an elongate portion and a sharpened tip portion, wherein the distal-most end of the tip portion of the moveable member is configured to penetrate tissue, and the moveable member includes a sharp edge extending along the elongate portion and the tip portion of the moveable member, and wherein the moveable member includes a plurality of openings in fluid communication with a hollow channel extending within the moveable member, wherein in the open position at least two of the plurality of openings are spaced on either side of a central longitudinal axis of the moveable member, wherein in the open position, the moveable member is configured to be received by and nest within the stationary member; and
receiving tissue within the moveable member.

9. The method of claim 8, wherein the stationary member includes a sharp edge extending along the elongate portion and the tip portion of the stationary member.

10. The method of claim 8, further including:
applying a pressure differential in the sampling portion via a pressure differential system, the pressure differential system being configured to form a pressure differential in the sampling portion when the sampling portion is in the open position.

11. The method of claim 10, wherein the moveable member includes a hollow channel therein, and wherein the pressure differential system is in fluid communication with the hollow channel of the moveable member.

12. The method of claim 8, wherein the moveable member includes a cross-sectional shape of a partial circle complimentary to a partial circle cross-sectional shape of the stationary member.

13. The method of claim 8, further including:
moving the sampling portion from the open position to the closed position and severing tissue.

14. A method of obtaining a tissue sample, comprising:
positioning a sampling portion of a biopsy device proximate target tissue, wherein the sampling portion is configured to receive and sever tissue, the sampling portion extending along a longitudinal axis;
moving the sampling portion from a closed position to an open position by rotating a moveable member relative to a stationary member about the longitudinal axis, the moveable member having a sharp edge, a hollow channel therein, and a plurality of apertures in fluid communication with the hollow channel, wherein in the open position at least two of the plurality of apertures are offset on either side of a central longitudinal axis of the moveable member, wherein in the open position, the moveable member is configured to be received by and nest within the stationary member, wherein the moveable member includes an elongate portion having a first diameter, and the stationary member includes an elongate portion having a second diameter, wherein the first diameter is different than the second diameter;

receiving tissue within the moveable member;

selectively applying a first pressure differential in the sampling portion in a direction substantially perpendicular to the longitudinal axis via a first pressure differential system, the first pressure differential system being configured to form a first pressure differential in the sampling portion when the sampling portion is in the open position, wherein the first pressure differential system is in fluid communication with the hollow channel and plurality of apertures of the moveable member; and selectively applying a second pressure differential in the sampling portion in a direction substantially parallel to the longitudinal axis via a second pressure differential system, the second pressure differential system being configured to form a second pressure differential in the sampling portion when the sampling portion is in the open position.

15. The method of claim 14, wherein each of the moveable and stationary members includes an elongate portion and a tip portion, wherein the moveable member includes a sharp edge extending along the elongate portion and the tip portion of the moveable member.

16. The method of claim 15, wherein the stationary member includes a sharp edge extending along the elongate portion and the tip portion of the stationary member.

17. The method of claim 16, wherein the tip portion of the moveable member is angled relative to the elongate portion of the moveable member, and wherein the tip portion of the stationary member is angled relative to the elongate portion of the stationary member.

18. The method of claim 14, further including:
moving the sampling portion from the open position to the closed position and severing tissue.

19. The method of claim 14, wherein the moveable member includes an elongate portion and a tip portion, wherein the tip portion of the moveable member is configured to pierce tissue.

* * * * *